United States Patent [19]
Duncombe et al.

[11] Patent Number: 6,002,031
[45] Date of Patent: Dec. 14, 1999

[54] METAL ALKOXYALKOXIDECARBOXYLATES AND USE TO FORM FILMS

[75] Inventors: Peter Richard Duncombe, Peekskill, N.Y.; Deborah Ann Neumayer, Danbury, Conn.

[73] Assignee: International Business Machines Corporation, Armonk, N.Y.

[21] Appl. No.: 09/148,613

[22] Filed: Sep. 4, 1998

[51] Int. Cl.$^6$ .............................. C07F 19/00; C07F 3/00; C07F 15/00
[52] U.S. Cl. ................................. 556/1; 556/42; 556/45; 556/54; 556/57; 556/81; 556/130; 556/146; 534/15; 427/372.2
[58] Field of Search .................................. 556/42, 45, 54, 556/76, 81, 130, 146, 57, 1; 534/15

[56] References Cited

U.S. PATENT DOCUMENTS

| | | | |
|---|---|---|---|
| 4,920,093 | 4/1990 | Nonaka et al. ............................ 505/1 |
| 5,138,520 | 8/1992 | McMillan et al. ........................ 361/31 |
| 5,328,718 | 7/1994 | Abe et al. ............................ 427/126.3 |
| 5,423,285 | 6/1995 | Paz de Araujo et al. ................. 117/90 |
| 5,454,861 | 10/1995 | Hasegawa et al. ......................... 106/2 |
| 5,456,945 | 10/1995 | McMillan et al. ...................... 427/252 |
| 5,514,822 | 5/1996 | Scott et al. ............................... 556/28 |
| 5,516,363 | 5/1996 | Azuma et al. ..................... 106/287.18 |
| 5,540,772 | 7/1996 | McMillan et al. ....................... 118/50 |
| 5,559,260 | 9/1996 | Scott et al. ............................... 556/28 |

*Primary Examiner*—Porfirio Nazario-Gonzalez
*Attorney, Agent, or Firm*—Pollock, Vande Sande & Amernick; Daniel P. Morris

[57] ABSTRACT

Metal alkoxyalkoxidecarboxylates wherein the alkoxy portion has 2–6 carbon atoms and the alkoxide portion has 2–6 carbon atoms are provided and are useful in forming films on a substrate.

25 Claims, No Drawings

METAL ALKOXYALKOXIDECARBOXYLATES AND USE TO FORM FILMS

DESCRIPTION

1. Technical Field

The present invention is concerned with novel metal alkoxyalkoxidecarboxylates and especially concerned with novel metal alkoxyalkoxidecarboxylates that can be used for fabricating thin films. Metal alkoxyalkoxidecarboxylate solutions of the present invention and especially mixtures of different metal alkoxyalkoxidecarboxylate solutions can be applied to a substrate and heated to form a metal oxide film. Metal oxide films formed according to the present invention find particular application as dielectric or ferroelectric layers in the microelectronics industry.

2. Background of Invention

Various metal oxide films have been suggested as dielectric or ferroelectric layers in the microelectronics industry. For instance, barium strontium titanate, lead zirconate titanate, barium titanate, strontium bismuth tantalate, strontium bismuth niobate, as well as other metal oxides have been suggested as the dielectric or ferroelectric capacitors used in memory cells. Metal oxide films such as barium strontium titanate (BST) or strontium bismuth tantalate (SBT) have many potential applications in dynamic random access memories (DRAM), nonvolatile random access memories (NVRAM), decoupling capacitor, passive component packaging (interposer) and gate insulator in field effect transistor (FET) display technology. Successful solution deposition of ferroelectrics or dielectrics such as BST or SBT depends on the availability of suitable precursors with appropriate reactivity, low cost, and nontoxicity.

For example, sol-gel deposition of BST and other dielectric or ferroelectric metal oxide materials is typically conducted with short-chain alkoxides such as ethoxides or isopropoxides. Short-chain alkoxides will absorb ambient water from the atmosphere, which quickly hydrolyzes some of the material and can lead to precipitate formation, thereby necessitating their handling and storage under inert atmospheres and limiting their shelf lives.

Other chemical solution deposition (CSD) routes to BST or SBT include metal-organic decomposition (MOD) routes based on thermal decomposition of metal carboxylates. Because of the chemical and thermal stability of metal carboxylates, removal of organics may require higher annealing temperatures and may pass through an oxocarbonate transition. An additional disadvantage of the chemical stability of metal carboxylates is their inability to undergo additional chemical reactions such as hydrolysis, condensation or chelation during processing, thereby restricting the ability to control thin film microstructures during heat treatment. For example, acetate based routes to BST typically require higher annealing temperature to convert oxocarbonate intermediates to barium strontium titanate. MOD routes to SBT typically employ long hot plate bake steps and high process temperatures (800° C.), and long anneal times (30–90 minutes), to completely remove organics from the coated films and to convert transitional phases to the desired strontium bismuth tantalate.

Such extreme processing conditions may degrade typical electrode stacks for dielectric and ferroelectric materials due to interfacial reactions, oxidation and dopant diffusion. Lowering of the processing temperature is highly desirable to stabilize these interlayers and to reduce electrode interaction problems. By combining the reactivity of metal alkoxides with the stability of metal carboxylates, lower process temperatures may be used to remove organic components in the film and the solutions may be stored, spun and handled without premature precipitation due to hydrolysis of the precursor components.

In previous work, the formation of the metal carboxylates from metal alkoxides and the corresponding acid required heating, multiple distillation steps and solvent exchange to ensure complete removal of any water which may have formed. The reaction of acid with alcohol may result in water formation, which may hydrolyze the starting materials, intermediates, or products, thereby creating precipitates and/or oligomers that are difficult to filter, that can upset the stoichiometry and that may decompose during heat treatment in an uncontrolled manner. It should be noted that others using the above-mentioned CSD process for producing electronic thin films have shown that these variables must be kept under careful control to eliminate cracking of the film, premature precipitation of CSD solutes before or during spinning of the film, and/or poor electrical properties of the film.

To avoid such problems complicated synthetic schemes have been devised involving multiple distillations to remove water and esters. To prevent further reaction, a solvent exchange is conducted with a higher boiling point solvent which necessitates additional prolonged distillation steps and consumption of large quantities of solvent, contributing to waste production. Other precautions include the use of hydrocarbon solvents such as octane or xylenes which are undesirable due to the reduced solubility of the polar metal species, especially highly electropositive elements such as Ba or Sr. Use of a co-solvent is required to prevent precipitation of strontium and barium solutes. In addition, xylene and octane are health and flammability hazards.

Thus, there is a need for a process that requires less time, less distillation, prevents precipitation or cloudiness of CSD solutions, and can be used to control the chemical nature of the desired product. In a previous disclosure, U.S. patent application Ser. No. 09/016,793, the disclosure of which is incorporated herein by reference, novel metal alkoxyalkoxides were disclosed. These novel metal alkoxyalkoxides are relatively water insensitive compared to short chain alkoxides and methoxymethoxides.

SUMMARY OF INVENTION

It has been found according to the present invention that in view of the relative water insensitivity of the metal alkoxyalkoxides of Ser. No. 09/016,793, they can be modified by addition of carboxylic acid without premature precipitation or cloudiness of the precursor solution. Addition of carboxylic acid allows the spinning of the solutions at greater molar concentrations resulting in thicker films per layer without formation of precipitates during storage, handling or spinning. Because the metal alkoxyalkoxides disclosed in U.S. Ser. No. 09/016,793 are relatively water insensitive, an additional benefit is gained by using a simplified synthetic scheme. Extensive distillations and/or a solvent exchange is unnecessary. The metal alkoxyalkoxidecarboxylates can be formed at room temperature from the metal alkoxyalkoxides and carboxylic acid. Solutions of the resultant metal alkoxyalkoxidecarboxylates have long shelf lives, are relatively insensitive to atmospheric humidity and water, and allow the spinning of thicker films without precipitation during spinning.

The present invention overcomes the problems outlined above by formation of a stable metal alkoxyalkoxidecarboxylate or mixtures of metal alkoxyalkoxidecarboxylates to form a liquid precursor solution capable of yielding metal oxides suitable for use in integrated circuits and other electronic components incorporating thin-film metal oxides.

The present invention relates to novel metal alkoxyalkoxidecarboxylates wherein the alkoxy moiety of the alkoxyalkoxide has 2 to 6 carbon atoms, the alkoxide moiety has 2 to 6 carbon atoms, and wherein the carboxylic acid has 2 to 18 atoms.

The novel metal alkoxyalkoxidecarboxylates can be presented by the molecular formula of $M(O(CH_2)_nOR)_x(A)_y$ where M=metal, n=2–6, x=1–5, y=1–5, R=alkoxy moiety, and A=carboxylic acid.

The metal alkoxyalkoxidecarboxylates can be synthesized by reacting metal alkoxyalkoxides with carboxylic acids. The reaction can be carried out at room temperature without heating. The novel metal alkoxyalkoxidecarboxylates of the present invention incorporate the reactivity of metal alkoxides to enable hydrolysis and condensation reactions during heating with the stability of metal carboxylates to prevent premature precipitation during storage, handling or spinning. Because the starting metal alkoxyalkoxides have superior water resistance compared to short chain alkoxides or methoxyethoxides, carboxylic acid can be added to them directly without forming precipitates thus allowing a simplified synthetic scheme with no heating, distillation or solvent exchange.

The present invention is also concerned with solutions of the metal alkoxyalkoxidecarboxylates.

Another aspect of the present invention is solutions of mixtures of metal alkoxyalkoxidecarboxylates of the present invention with each other and/or with other metal alkoxyalkoxidecarboxylates.

A further aspect of the invention is forming films from solutions of the metal alkoxyalkoxidecarboxylates.

Still other objects and advantages of the present invention will become readily apparent by those skilled in the art from the following detailed description, wherein it is shown and described only the preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

BEST AND VARIOUS MODES FOR CARRYING OUT INVENTION

The present invention relates to novel metal alkoxyalkoxidecarboxylates. Metal alkoxyalkoxidecarboxylates of the present invention exhibit a combination of sufficient reactivity to enable hydrolysis and condensation reactions during heating while at the same time exhibiting the stability needed to prevent premature precipitation during storage, handling or spinning.

According to the present invention, the alkoxy portion of metal alkoxyalkoxidecarboxylate contains 2–6 carbon atoms and includes ethoxy, propoxy, butoxy, pentoxy and heptoxy moieties with butoxy being preferred.

The alkoxide portion of the compounds of the present invention contains 2–6 carbon atoms, preferably 2–3 carbon atoms, and includes ethanol and propanol.

Examples of suitable alkoxyalkoxide portions of the compounds of the present invention are ethoxyethanol, propoxyethanol, butoxyethanol, pentoxyethanol, heptoxyethanol, ethoxypropanol, propoxypropanol, butoxypropanol, pentoxypropanol, and heptoxypropanol, and preferably butoxyethanol.

Typical metals employed to form the novel alkoxyalkoxides of the present invention are metals selected from the group consisting of Group I, Group II, Group IIIA, Group IIIB, Group IVA, Group IVB, Group V, Group VIIB and Group VIII metals.

Examples of suitable Group I metals include the Group IA alkali metals Li, Na and K; and the Group IB metals such as Cu.

Examples of suitable Group II metals include the Group IIA alkaline earth metals Mg, Ca, Sr and Ba; and Group IIB metals such as Zn.

Examples of suitable Group IIIA metals are Al and Ga.

Examples of suitable Group IIIB metals are Sc, Y and La.

An example of a suitable group IVA metal is Pb.

Examples of suitable Group IVB metals are Ti and Zr.

Examples of suitable Group V metals are Group VB metals such as Nb and Ta and Group VA metals such as Bi.

An example of a Group VIIB metal is Mn.

Examples of Group VIII metals are Fe, Ru, Co, Ni and Rh.

The preferred metals are the alkali metals, alkaline earth metals, Nb, Pb, Ta and Bi and most preferably Bi, Ba, Sr, Nb, Ta, Pb, Ti and Zr.

The carboxylic acids typically contain 2 to 18 carbon atoms, examples of which being acetic acid, propanoic acid, butanoic acid, ethylhexanoic acid and neodecandoic acid with ethylhexanoic being preferred.

The following are some examples of alkoxyalkoxidecarboxylates according to the present invention:

ethylhexanoate of Barium (butoxyethoxide)$_2$
ethylhexanoate of Strontium (butoxyethoxide)$_2$
ethylhexanoate of Tantalum (butoxyethoxide)$_5$
ethylhexanoate of Bismuth (butoxyethoxide)$_3$
ethylhexanoate of Niobium (butoxyethoxide)$_5$
ethylhexanoate of Titanium (butoxyethoxide)$_4$
ethylhexanoate of Zirconium (butoxyethoxide)$_4$
ethylhexanoate of Vanadium (butoxyethoxide)$_5$
ethylhexanoate of Lead (butoxyethoxide)$_2$
ethylhexanoate of Ruthenium (butoxyethoxide)$_4$
ethylhexanoate of Tantalum (butoxyethoxide)$_5$
ethylhexanoate of Lanthanum (butoxyethoxide)$_3$
ethylhexanoate of Cobalt (butoxyethoxide)$_2$.

The following represent some examples of solutions containing carboxylate of at least three metal alkoxyalkoxides.

Carboxylate of strontium (butoxyethoxide)$_2$, bismuth (butoxyethoxide)$_3$ and tantalum (butoxyethoxide)$_5$.

Carboxylate of barium (butoxyethoxide), zirconium (butoxyethoxide)$_4$ and titanium (butoxyethoxide)$_4$.

Carboxylate of strontium (butoxyethoxide)$_2$, barium (butoxyethoxide)$_2$, and titanium (butoxyethoxide)$_4$.

Carboxylate of lead (butoxyethoxide)$_2$, zirconium (butoxyethoxide)$_4$ and titanium (butoxyethoxide)$_4$.

Carboxylate of lanthanum (butoxyethoxide)$_3$, strontium (butoxyethoxide)$_2$ and cobalt (butoxyethoxide)$_2$.

Carboxylate of strontium (butoxyethoxide)$_2$, tantalum (butoxyethoxide)$_4$, and niobium (butoxyethoxide)$_4$.

The following represents exemplary solutions that contain carboxylate of at least four metal alkoxyalkoxides.

Carboxylate of lead (butoxyethoxide)$_2$, lanthanum (butoxyethoxide)$_3$, zirconium (butoxyethoxide)$_4$ and titanium (butoxyethoxide)$_4$.

Carboxylate of strontium (butoxyethoxide)$_2$, bismuth (butoxyethoxide)$_3$, titanium (butoxyethoxide)$_4$ and tantalum (butoxyethoxide)$_4$.

Carboxylate of strontium (butoxyethoxide)$_2$, bismuth (butoxyethoxide)$_3$, titanium (butoxyethoxide)$_4$ and niobium (butoxyethoxide)$_4$.

Carboxylate of strontium (butoxyethoxide)$_2$, bismuth (butoxyethoxide), tantalum (butoxyethoxide)$_4$ and niobium (butoxyethoxide)$_4$.

The metal alkoxyalkoxides employed in synthesizing the alkoxyalkoxidecarboxylates of the present invention can be prepared by the procedure disclosed in Ser. No. 09/016,793. In particular, the metal alkoxyalkoxides can be synthesized by reacting the metal with an excess of the alkoxyalcohol, or by reacting a metal alkoxide with an excess of alkoxyalcohol or by reacting a metal halide salt with the lithium, sodium or potassium salt of the alkoxyalcohol. The reaction is typically carried out in a miscible solvent. Miscible solvents that may be used include hydrocarbons such as xylene, toluene, halogenated solvents such as chloroform; alcohols such as methanol, ethanol, isopropanol, methoxyethanol, ethoxyethanol, propoxyethanol, butoxyethanol, pentoxyethanol, heptoxyethanol, methoxypropanol, ethoxypropanol, propoxypropanol, butoxypropanol, pentoxyproponal, and heptoxyproponal, preferably butoxyethanol; and oxygenated solvents such as ethyl ether and butyl acetate.

For example, when an alkali earth (Group IA: Li, Na, K) metal or an alkaline earth (Group IIA: Mg, Ca, Sr, Ba) metal is added to an excess of alkoxyalcohol and heated, the following reaction occurs:

$$M+L \rightarrow ML_a + \tfrac{1}{2}H_2. \tag{1}$$

When a metal alkoxide is added to an excess of alkoxyalcohol and heated the following reaction occurs where A is an alkoxide:

$$MA_a + L \rightarrow ML_a + aA. \tag{2}$$

When a sufficiently reactive metal halide salt is added to an alkali earth metal (Group IA: Li, Na, K) salt of the alkoxyalcohol and heated, the following reactions occurs, where X is a halide, and N is alkali earth metal (Group IA: Li, Na, K):

$$MX_a + aNL \rightarrow ML_a + aNX. \tag{3}$$

The metal alkoxyalkoxide is then reacted with the carboxylic acid typically at room temperature.

The metal alkoxyalkoxidecarboxylates of the present invention are especially suitable for forming films on a substrate. Once the metal alkoxyalkoxidecarboxylate is formed, it can be dissolved into a miscible solvent such as those disclosed above and applied to a substrate. The coated substrate is thermally treated to densify the film. The coated substrate may be annealed to crystallize the film.

The substrate is typically heated to temperatures of about 200° C. to about 500° C., and more typically about 300° C. to about 400° C., for about 1 to about 15 minutes to densify the film. The annealing is typically carried out at temperatures of about 500° C. to about 800° C., and more typically about 650° C. to about 750° C. for about 1 to about 60 minutes to crystallize the film.

According to preferred aspects of the present invention, mixtures of the metal alkoxyalkoxidecarboxylates with each other and/or with metal alkoxides are employed to create mixed metal oxide layers. Preferably, such alkoxyalkoxides contain 2–6 carbon atoms in the alkoxy moiety and 2–6 in the alkoxide moiety.

The carboxylates are typically present in the solution in amounts of about 0.01 molar to about 3 molar and preferably about 0.1 molar to about 1 molar.

The following non-limiting examples are presented to further illustrate the present invention.

EXAMPLE 1

Preparation of Ba(butoxyethoxide)$_2$

Under nitrogen, 25.2 g barium metal is added to 111 grams of butoxyethanol. The slurry is refluxed for 1 h to complete the reaction. The solution was cooled to room temperature, and filtered through a celite bed in vacuo. The filtrate is the barium butoxyethoxide stock solution with a concentration of 1.42 moles/liter or 22.69 weight percent of barium.

EXAMPLE 2

Preparation of Sr(butoxyethoxide)$_2$

Under nitrogen 26.1 g strontium metal is added to 293 g of butoxyethanol. The slurry is refluxed for 1 h to complete the reaction. The solution is cooled to room temperature, and filtered through a celite bed in vacuo. The filtrate is the strontium butoxyethoxide stock solution with a concentration of 0.919 moles/liter or 8.92 weight percent of strontium.

EXAMPLE 3

Preparation of Ta(butoxyethoxide)$_5$

Under nitrogen with stirring, 53.13 g tantalum (V) ethoxide is added to 150 ml of butoxyethanol. The ethanol is distilled away and an additional 50 ml of butoxyethanol is added and refluxed for 1 h. The solution is cooled to room temperature, and filtered through a celite bed in vacuo. The filtrate is the tantalum butoxyethoxide stock solution.

EXAMPLE 4

Preparation of Bi(butoxyethoxide)$_3$

Under inert atmosphere, 28.9 g (0.244 mol) of butoxyethanol is added drop wise to a stirring suspension of 9.45 g (0.394 mol) sodium hydride in 100 mL of tetrahydrofuran. After stirring for 30 minute, the slurry is filtered through a celite bed. To the filtrate is added 25.0 g (0.0793 mol) of BiCl$_3$ dissolved in 100 ml of tetrahydrofuran. After stirring for 12 h, the tetrahydrofuran is removed in vacuo resulting in a cloudy yellow slurry which is extracted with 250 ml of anhydrous toluene. The extract is filtered through a celite bed. The toluene is removed from the filtrate in vacuo resulting in a pale yellow oil which is extracted with 500 ml of pentane. The pentane extract is filtered through a celite bed and the pentane removed from the filtrate in vacuo resulting in a pale yellow liquid.

EXAMPLE 5

Preparation of Bi(butoxyethoxide)$_3$

Under nitrogen with stirring, 20 g bismuth (III) t-pentoxide is added to 50 ml of butoxyethanol. The t-pentanol is distilled away and an additional 50 ml of butoxyethanol is added and refluxed for 1 h. The solution is cooled to room temperature, and filtered through a celite bed in vacuo. The filtrate is the bismuth butoxyethoxide stock solution with a final concentration of 0.4 moles/liter of bismuth.

EXAMPLE 6

Preparation of Bi(ethylhexanoate)$_3$

Under nitrogen, 0.15 mol of ethylhexanoic acid is added to 0.05 mol of bismuth butoxyethoxide (example 5 or 6) in butoxyethanol. The resultant solution is filtered resulting in a 13.84 weight percent of bismuth in solution.

EXAMPLE 7

Preparation of Zr(butoxyethoxide)$_4$

Under nitrogen, 110 g zirconium (IV) isopropoxide is added to 100 ml of butoxyethanol. The isopropanol is distilled away and an additional 100 ml of butoxyethanol is added and refluxed for 1 h. The solution is cooled to room temperature, and filtered through a celite bed in vacuo. The filtrate is the zirconium butoxyethoxide stock solution.

EXAMPLE 8

Preparation of Nb(butoxyethoxide)$_5$

Under nitrogen with stirring, 52.77 g niobium (V) ethoxide is added to 150 ml of butoxyethanol. The ethanol is distilled away and an additional 50 ml of butoxyethanol is added and refluxed for 1 h. The solution is cooled to room temperature, and filtered through a celite bed in vacuo. The filtrate is the niobium butoxyethoxide stock solution with a final concentration of 1.127 moles/liter or 9.75 weight percent of niobium.

EXAMPLE 9

Preparation of Ti(butoxyethoxide)$_4$

Under nitrogen, 110 g titanium (IV) isopropoxide is added to 100 ml of butoxyethanol. The isopropanol is distilled away and an additional 100 ml of butoxyethanol is added and refluxed for 1 h. The solution is cooled to room temperature, and filtered through a celite bed in vacuo. The filtrate is the titanium butoxyethoxide stock solution with a final concentration of 1.53 moles/liter or 7.91 weight percent of titanium.

EXAMPLE 10

Preparation of Ethylhexanoate of Bismuth and Titanium Butoxyethoxides and Fabrication of a Bi$_4$Ti$_3$O$_{12}$ Film Therefrom Under nitrogen, 0.02 mol of a bismuth butoxyethoxide (example 5) and 0.015 mol of a titanium butoxyethoxide (example 9) are mixed together, before addition of 0.06 mol of ethylhexanoic acid. The solution is stirred overnight at room temperature, filtered, and diluted to 100 mL with butoxyethanol. The solution is loaded into a syringe and a 0.45 $\mu$m and 0.1 $\mu$m Whatman syringe filters are attached. The solution is syringed onto Pt/Ti/SiO$_2$/Si substrate until the substrate is completely wetted. The substrate is then spun for 60 sec at 2500 rpm. The coated substrate is dried on a hot plate at 350° C. Additional layers are deposited to fabricate thicker films. The coated substrate is then annealed by rapid thermal processing at 700° C. for 2 minutes.

EXAMPLE 11

Preparation of Ethylhexanoate of Zirconium, Titanium and Barium Butoxyethoxides and Fabrication of a Ba(Zr$_{0.5}$Ti$_{0.5}$)O$_3$ Film Therefrom Under nitrogen, 3.2 g (0.00825 mol) zirconium isopropoxide is mixed with 17.21 g (0.0605 mol) of titanium isopropoxide, and 60 ml of butoxyethanol. The solution is refluxed and isopropanol is distilled away. The solution is allowed to cool to room temperature. In a separate flask, 60 ml of butoxyethanol is added to 9.446 g (0.0688mol) of Barium metal. The suspension is heated gently for 2 h until the barium metal is completely consumed. After the reaction is complete the solution is allowed to cool to room temperature. Under nitrogen, the zirconium and titanium solution is added to the barium solution and stirred. After 1 h, 19.8 g (0.138 mol) of ethylhexanoic acid is added to the combined barium, zirconium and titanium solution and stirred overnight at room temperature. The solution is filtered through a celite bed and medium porosity frit. The solution is loaded into a syringe and 0.45 $\mu$m and 0.1 $\mu$m Whatman syringe filters are attached. The solution is syringed onto Pt/Ti/SiO$_2$/Si substrate until the substrate is completely wetted. The substrate is then spun for 60 sec at 2500 rpm. The coated substrate is dried on a hot plate at 350° C. and then annealed in O$_2$ at 700° C. for 10 min. Additional layers are deposited to fabricate thicker films.

EXAMPLE 12

Preparation of Ethylhexanoate of Strontium, Tantalum and Niobium Butoxyethoxides and Fabrication of a Sr(Ta$_{0.7}$Nb$_{0.3}$)$_2$O$_7$ Film Therefrom Under nitrogen, 0.031 mol of tantalum butoxyethoxide (example 3) and 0.0133 mol of niobium butoxyethoxide (example 8) are mixed together. In a separate flask, 30 ml of butoxyethanol is added to 3.90 g (0.0445 mol) of Strontium metal. The suspension is heated gently for 2 h until the strontium metal is completely consumed. After the reaction is complete the solution is allowed to cool to room temperature. Under nitrogen, the tantalum and niobium solution is added to the strontium solution and stirred. After 1 h, 12.8 g (0.0898 mol) of ethylhexanoic acid is added to the combined strontium tantalum and niobium solution and stirred overnight. The solution is filtered through a celite bed and medium porosity frit. The solution is loaded into a syringe and 0.45 $\mu$m and 0.1 $\mu$m Whatman syringe filters are attached. The solution is syringed onto Pt/Ti/SiO$_2$/Si substrate until the substrate is completely wetted. The substrate is then spun for 60 sec at 2500 rpm. The coated substrate is dried on a hot plate at 350° C. and then rapidly thermally annealed in O$_2$ at 1000° C. for 10 sec. Additional layers are deposited to fabricate thicker films.

EXAMPLE 13

Preparation of Ethylhexanoate of Strontium and Tantalum Butoxyethoxides and Bismuth Ethylhexanoate and Fabrication of a Sr$_{0.85}$Bi$_{2.2}$Ta$_2$O$_9$ Film Therefrom Under nitrogen, 0.015 mol of strontium butoxyethoxide (example 2), 0.035 mol of tantalum butoxyethoxide (example 3), and 0.039 mol of bismuth ethylhexanoate (example 6) are mixed at room temperature. The solution is stirred overnight, filtered and diluted to 100 g. The solution is loaded into a syringe and 0.45 µm and 0.1 µm Whatman syringe filters are attached. The solution is syringed onto Pt/SiO$_2$/Si substrate until the substrate is completely wetted. The substrate is then spun for 60 sec at 2500 rpm. The coated substrate is dried on a hot plate at 400° C. and then rapidly thermally annealed in O$_2$ at 725° C. for 30 sec. Three additional layers are deposited to fabricate thicker films. A final furnace anneal is conducted at 800° C. for 60 m. The film is 194 nm thick. Pt electrodes are deposited and a post electrode anneal is conducted at 800° C. for 2 m. The resultant film has a Pr of 7.4 µC/cm$^2$ at 3V with 10$^{-7}$ A/cm$^2$ leakage current.

EXAMPLE 14

Preparation of Ethylhexanoate of Strontium, Tantalum and Bismuth Butoxyethoxides and Fabrication of a Sr$_{0.8}$Bi$_{2.2}$Ta$_2$O$_9$ Film Therefrom Under nitrogen, 0.014 mol of strontium butoxyethoxide (example 2), 0.036 mol of tantalum butoxyethoxide (example 3), and 0.040 mol of bismuth butoxyethoxide (example 5) are mixed at room temperature, then 0.040 mol of ethylhexanoic acid is added. The solution is stirred overnight at room temperature, filtered and diluted to 50 ml. The solution is loaded into a syringe and a 0.45 µm and 0.1 µm Whatman syringe filters are attached. The solution is syringed onto Pt/SiO$_2$/Si substrate until the substrate is completely wetted. The substrate is then spun for 60 sec at 2500 rpm. The coated substrate is dried on a hot plate at 350° C. and then rapidly thermally annealed in O$_2$ at 700° C. for 10 sec. Additional layers are deposited to fabricate thicker films. A final furnace anneal is conducted at 800° C. for 60 m.

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:

1. A metal alkoxyalkoxidecarboxylate wherein the alkoxy moiety of said alkoxyalkoxide has 2 to 6 carbon atoms, wherein the alkoxide moiety has 2 to 6 carbon atoms, and wherein the carboxylate moiety has 2 to 18 carbon atoms.

2. The metal alkoxyalkoxidecarboxylate of claim 1 wherein the metal comprises at least one metal selected from the group consisting of Group I, Group II, Group IIIA, Group IIIB, Group IVA, Group IVB, Group V, Group VIIB and Group VIII.

3. The metal alkoxyalkoxidecarboxylate of claim 1 wherein the metal comprises at least one metal selected from the group consisting of Group I, Group II, Group IIIB, Group IVA, Group V, Group VIIB and Group VIII.

4. The metal alkoxyalkoxidecarboxylate of claim 1 wherein the alkoxy moiety is selected from the group consisting of ethoxy, propoxy, butoxy, pentoxy and heptoxy.

5. The metal alkoxyalkoxidecarboxylate of claim 1 wherein the alkoxy moiety is butoxy.

6. The metal alkoxyalkoxidecarboxylate of claim 1 wherein the alkoxide moiety is from ethanol and propanol.

7. The metal alkoxyalkoxidecarboxylate of claim 1 wherein the alkoxyalkoxide portion is an alcohol selected from the group consisting of ethoxyethanol, propoxyethanol, butoxyethanol, pentoxyethanol, heptoxyethanol, ethoxypropanol, propoxypropanol, butoxypropanol, pentoxypropanol and heptoxypropanol.

8. The metal alkoxyalkoxidecarboxylate of claim 1 obtained from butoxyethanol.

9. The metal alkoxyalkoxidecarboxylate of claim 1 wherein the carboxylate moiety is from at least one carboxylic acid selected from the group consisting of acetic, propanoic, butanoic, ethylhexanoic and neodecandoic.

10. The metal alkoxyalkoxidecarboxylate of claim 9 wherein the carboxylic acid comprises ethylhexanoic acid.

11. The metal alkoxyalkoxidecarboxylate of claim 1 wherein the metal is selected from the group consisting of alkali metal, alkaline earth metal, Nb, Pb, Ta, Bi, Ti lanthanides, Zn, Cr, Co, Mn, Fe, Ni, Hf, V, W, Zr and Tl.

12. The metal alkoxyalkoxidecarboxylate of claim 1 wherein the metal is selected from the group consisting of Bi, Pb, Ba and Sr.

13. The metal alkoxyalkoxidecarboxylate of claim 1 being ethylhexanoate of Ba(butoxyethoxide)$_2$.

14. The metal alkoxyalkoxidecarboxylate of claim 1 being ethylhexanoate of Sr(butoxyethoxide)$_2$.

15. The metal alkoxyalkoxidecarboxylate of claim 1 being ethylhexanoate of Ta(butoxyethoxide)$_5$.

16. The metal alkoxyalkoxidecarboxylate of claim 1 being ethylhexanoate of Bi(butoxyethoxide)$_3$.

17. The metal alkoxyalkoxidecarboxylate of claim 1 being ethylhexanoate of Nb(butoxyethoxide)$_5$.

18. The metal alkoxyalkoxidecarboxylate of claim 1 being ethylhexanoate of titanium (butoxyethoxide)$_4$.

19. The metal alkoxyalkoxide carboxylate of claim 1 being ethylhexanoate of zirconium (butoxyethoxide)$_4$.

20. The metal alkoxyalkoxidecarboxylate of claim 1 being ethylhexanoate of vanadium (butoxyethoxide)$_5$.

21. The metal alkoxyalkoxidecarboxylate of claim 1 being ethylhexanoate of lead (butoxyethoxide)$_2$.

22. The metal alkoxyalkoxidecarboxylate of claim 1 being ethylhexanoate of ruthenium (butoxyethoxide)$_4$.

23. The metal alkoxyalkoxidecarboxylate of claim 1 being ethylhexanoate of tantalum (butoxyethoxide)$_5$.

24. The metal alkoxyalkoxidecarboxylate of claim 1 being ethylhexanoate of lanthanum (butoxyethoxide)$_3$.

25. The metal alkoxyalkoxidecarboxylate of claim 1 being ethylhexanoate of cobalt (butoxyethoxide)$_2$.

* * * * *